United States Patent
Rothschild

(10) Patent No.: US 8,842,808 B2
(45) Date of Patent: Sep. 23, 2014

(54) SCATTER ATTENUATION TOMOGRAPHY USING A MONOCHROMATIC RADIATION SOURCE

(75) Inventor: Peter J. Rothschild, Newton, MA (US)

(73) Assignee: American Science and Engineering, Inc., Billerica, MA (US)

(*) Notice: Subject to any disclaimer, the term of this patent is extended or adjusted under 35 U.S.C. 154(b) by 761 days.

(21) Appl. No.: 13/164,039

(22) Filed: Jun. 20, 2011

(65) Prior Publication Data

US 2011/0249798 A1    Oct. 13, 2011

Related U.S. Application Data

(63) Continuation-in-part of application No. 12/488,635, filed on Jun. 22, 2009, now Pat. No. 7,995,707, which is a continuation of application No. 11/834,888, filed on Aug. 7, 2007, now Pat. No. 7,555,099.

(60) Provisional application No. 60/822,162, filed on Aug. 11, 2006.

(51) Int. Cl.
  *G01N 23/04* (2006.01)
  *G01N 23/20* (2006.01)
  *G01N 23/203* (2006.01)
  *G01V 5/00* (2006.01)

(52) U.S. Cl.
  CPC ........ *G01N 23/046* (2013.01); *G01N 23/20083* (2013.01); *G01N 23/203* (2013.01); *G01V 5/0025* (2013.01)
  USPC .......................................................... 378/86

(58) Field of Classification Search
  CPC ............................. G01V 5/0025; A61B 6/483
  USPC .................... 378/86, 70, 87, 88, 62
  See application file for complete search history.

(56) References Cited

U.S. PATENT DOCUMENTS

| 2,670,401 A | 2/1954 | Weinberg .................. 178/6.8 |
| RE28,544 E | 9/1975 | Stein et al. ................. 250/369 |

(Continued)

FOREIGN PATENT DOCUMENTS

| DE | 26 39 631 | 3/1978 | ............. A61B 6/02 |
| DE | 197 10 222 | 9/1998 | ............. H01J 37/30 |
| SU | 448413 | 11/1974 | ............. G01N 23/02 |

OTHER PUBLICATIONS

Harding, "On the Sensitivity and Application Possibilities of a Novel Compton Scatter Imaging System", *IEEE Transactions on Nuclear Science*, vol. NS-29, No. 3, pp. 1260- 1265 (Jun. 1982).

(Continued)

*Primary Examiner* — Irakli Kiknadze
(74) *Attorney, Agent, or Firm* — Sunstein Kann Murpy & Timbers LLP

(57) ABSTRACT

A system and methods for characterizing an inspected object on the basis of attenuation between identified regions of scattering and a plurality of detectors. An incident beam of substantially monochromatic penetrating radiation is generated by a source, which may be a radioactive source. The incident beam is characterized by a propagation axis and a source energy. Radiation scattered by the object is detected by means of a plurality of detector elements disposed about the beam of penetrating radiation, each detector element generating a detector signal characterizing a detected energy of scattered radiation. The detector signal provides for determining a displacement for each scattering point of the object relative to a fiducial position on the propagation axis of the incident beam, based upon the detected energy of the scattered radiation. By calculating the attenuation of penetrating radiation between pairs of scattering voxels, a tomographic image is obtained characterizing the three-dimensional distribution of attenuation in the object of one or more energies of penetrating radiation, and thus of material characteristics.

15 Claims, 4 Drawing Sheets

(56) References Cited

U.S. PATENT DOCUMENTS

| | | | |
|---|---|---|---|
| 3,955,089 A | 5/1976 | McIntyre et al. | 250/399 |
| 4,002,917 A | 1/1977 | Mayo | 250/445 T |
| 4,144,457 A | 3/1979 | Albert | 250/445 T |
| 4,149,076 A | 4/1979 | Albert | 250/402 |
| 4,194,123 A | 3/1980 | Wittry | 250/492 A |
| 4,196,351 A | 4/1980 | Albert | 250/416 TV |
| 4,357,535 A | 11/1982 | Haas | 378/57 |
| 4,535,243 A | 8/1985 | Peschmann | 250/363 S |
| 4,598,415 A | 7/1986 | Luccio et al. | 378/119 |
| 4,672,615 A | 6/1987 | Kelly et al. | 372/2 |
| 4,694,457 A | 9/1987 | Kelly et al. | 372/2 |
| 4,730,350 A | 3/1988 | Albert | 378/10 |
| 4,799,247 A | 1/1989 | Annis et al. | 378/87 |
| 4,864,142 A | 9/1989 | Gomberg | 250/390.04 |
| 4,868,856 A | 9/1989 | Frith et al. | 378/86 |
| 4,884,289 A | 11/1989 | Glockmann et al. | 378/57 |
| 5,022,062 A | 6/1991 | Annis | 378/86 |
| 5,097,492 A | 3/1992 | Baker et al. | 378/22 |
| 5,153,900 A | 10/1992 | Nomikos et al. | 378/65 |
| 5,179,581 A | 1/1993 | Annis | 378/57 |
| 5,181,234 A | 1/1993 | Smith | 378/87 |
| 5,182,764 A | 1/1993 | Peschmann et al. | 378/57 |
| 5,247,561 A | 9/1993 | Kotowski | 378/87 |
| 5,260,982 A | 11/1993 | Fujii et al. | 378/87 |
| 5,313,511 A | 5/1994 | Annis et al. | 378/87 |
| 5,420,905 A | 5/1995 | Bertozzi | 378/88 |
| 5,430,787 A | 7/1995 | Norton | 378/87 |
| 5,442,678 A | 8/1995 | Dinsmore et al. | 378/137 |
| 5,504,796 A | 4/1996 | Da Silveira et al. | 378/121 |
| 5,548,630 A | 8/1996 | Hell et al. | 378/137 |
| 5,642,394 A | 6/1997 | Rothschild | 378/57 |
| 5,682,412 A | 10/1997 | Skillicorn et al. | 378/98.6 |
| 5,696,806 A | 12/1997 | Grodzins et al. | 378/86 |
| 5,712,889 A | 1/1998 | Lanzara et al. | 378/19 |
| 5,805,662 A | 9/1998 | Kurbatov et al. | 378/87 |
| 5,841,831 A | 11/1998 | Hell et al. | 378/19 |
| 5,930,326 A | 7/1999 | Rothschild et al. | 378/57 |
| 5,995,586 A | 11/1999 | Jahnke | 378/137 |
| 6,111,974 A | 8/2000 | Hiraoglu et al. | 382/100 |
| RE37,899 E | 11/2002 | Grodzins et al. | 378/86 |
| 6,563,906 B2 * | 5/2003 | Hussein et al. | 378/89 |
| 7,203,276 B2 | 4/2007 | Arsenault et al. | 378/87 |
| 7,412,022 B2 * | 8/2008 | Jupiter et al. | 378/2 |
| 2001/0046275 A1 | 11/2001 | Hussein | 378/7 |
| 2006/0043310 A1 * | 3/2006 | Arsenault et al. | 250/393 |

OTHER PUBLICATIONS

Murphy, "A rising war on terrorists", *IEEE Spectrum*, pp. 33-36 (Nov. 1989).

Stein et al., "Flying Spot X-Ray Imaging Systems", *American Science and Engineering, Inc.*, ASE-2864, 21 pages. (Dec. 1971).

Stein et al., "Flying Spot X-Ray Imaging Systems", Materials Evaluation, *An Official Journal of the American Society of Nondestructive Testing*, vol. XXX, No. 7, pp. 137-141 and 148 (Jul. 1972).

Stein, "X-Ray Imaging with a Scanning Beam", *Radiology*, vol. 117, pp. 713-716 (Dec. 1975).

Towe et al., "X-Ray Compton Scatter Imaging Using a High Speed Flying Spot X-Ray Tube", *IEEE Trans. on Biomed. Eng.*, vol. BME-28, No. 10, pp. 717-721 (Oct. 1981).

Tracy, E.J., "A New X-Ray Scanner to Hinder Hijackers", *Fortune*, p. 146 (Apr. 1986).

\* cited by examiner

SCATTER ATTENUATION TOMOGRAPHY USING A MONOCHROMATIC RADIATION SOURCE

The present application is a continuation-in-part of copending U.S. patent application Ser. No. 12/488,635, filed Jun. 22, 2009, a continuation of U.S. Ser. No. 11/834,888, which issued, on Jun. 30, 2009, as U.S. Pat. No. 7,555,099. Like the two foregoing applications, the present application claims priority from U.S. Provisional Patent Application Ser. No. 60/822,162, filed Aug. 11, 2006. All of the foregoing prior applications are incorporated herein by reference.

TECHNICAL FIELD

The present invention relates to methods and systems for inspecting objects by means of penetrating radiation, whereby entire volumes of an object may be characterized on the basis of attenuation of the penetrating radiation between scattering points identified by methods of the invention.

BACKGROUND OF THE INVENTION

In the period since September, 2001, X-Ray Computerized Tomography (CT) has been used extensively to search for explosive materials concealed in airline baggage. The method works by measuring the "CT number" of objects contained in a suitcase. The CT number is essentially a measure of the attenuation per unit length of x-rays (with a given energy distribution) in the material comprising each object. The CT number can then be used to identify the material. As a matter of definition, "CT number," as used herein and in any appended claims, will refer to a measure of x-ray attenuation, conventionally quoted relative to the attenuation of water.

For organic materials, the CT number is essentially a measure of the electron density of the material, which in turn, is proportional to the mass density. X-Ray CT systems are therefore able to measure the mass density of concealed materials. Explosive materials tend to have mass densities which lie in the range of about 1.2-1.7 grams per cubic centimeter (g/cc). Since x-Ray CT systems reconstruct the contents of a container in three dimensions, the volume of each concealed object is also determined. Combining this information with the density yields the mass of each object. By selecting objects with a minimum size and mass which have a density between 1.2 and 1.7 g/cc, explosive threats can automatically be detected in the container, and an alarm sounded.

Disadvantages of x-Ray CT systems include their size and cost. Both the size and cost arise largely because of the rapidly rotating gantries on which the x-ray source and detector arrays are mounted.

U.S. Pat. No. 5,930,326, entitled "Side Scatter Tomography System," described a method for detecting radiation scattered at essentially 90 degrees out of a raster-scanning pencil beam of x-rays, as detected by one or more arrays of segmented and collimated detector arrays. The intensity distribution of the side-scattered radiation is then used to reconstruct (in three dimensions) the organic objects concealed within a container. That patent is incorporated herein by reference.

The concept of Scatter Attenuation Tomography (SAT) has been previously described in U.S. Pat. Nos. 7,551,718 and 7,924,979, both of which are incorporated herein by reference. The '718 and '979 patents make use of one or more collimated scatter detectors to measure the attenuation of scatter within a concealed object or material. For example, a recent application of SAT has been to identify liquids for aviation security to ensure that no flammable, explosive, or explosive precursor liquids can be brought onto aircraft. The limitation of the SAT concept described in the '718 and '979 patents is that it is essentially a point interrogation technique which characterizes the density and effective atomic number of a single volume element or "voxel" of the object being inspected. This is because the measurement is typically made in the sub-volume defined by the intersection of the x-ray beams and the field of view of a pair of collimated scatter detectors. The location of the sub-volume of interest must therefore be known beforehand, and the system must be either moved or oriented so that this volume is being interrogated. This can be problematic if the precise location of a suspect sub-volume is not known. Another limitation of the SAT technique previously described is that in order to characterize the material in more than one sub-volume, an array of collimated scatter detectors must be used, adding considerable expense and complexity.

SUMMARY OF THE INVENTION

In accordance with preferred embodiments of the present invention, methods and a system are provided for characterizing an object in terms of x-ray attenuation. One embodiment of such an x-ray inspection system has a source for generating an incident beam of substantially monochromatic penetrating radiation, where the incident beam is characterized by a propagation axis and a source energy. The system also has a plurality of detector elements disposed about the beam of penetrating radiation, each detector element generating a detector signal characterizing a detected energy of scattered radiation. Finally, the system has a processor input adapted to receive the detector signal characterizing radiation scattered from at least one scattering point of the object illuminated by the incident beam, and a processor adapted to determine a displacement for each scattering point of the object relative to a fiducial position on the propagation axis of the incident beam on a basis of the detected energy of the scattered radiation.

In accordance with other embodiments of the present invention, the processor is further adapted to characterize the object on the basis of a measure of attenuation between an identified scattering point and an identified detector. The source for generating an incident beam may be a radioactive source, and a beam steerer may be provided for varying at least one of an orientation and a position of the incident beam relative to the object. The beam steerer may include a moving shutter, as well as an actuator for moving the source.

In further embodiments of the present invention, at least one of a plurality of detector elements may be disposed to the side of the object with respect to the incident beam, and the detector elements may be energy-selective.

In an alternate embodiment of the present invention, a method is provided for characterizing an object on the basis of a measure of attenuation in a direction having a transverse component to an incident beam. The method has processes of:

generating an incident beam of substantially monochromatic penetrating radiation, the incident beam characterized by a propagation axis and a source energy;

detecting radiation scattered by the object by means of a plurality of detector elements disposed about the beam of penetrating radiation, each detector element generating a detector signal characterizing a detected energy of scattered radiation;

receiving the detector signal characterizing radiation scattered from at least one scattering point of the object illuminated by the incident beam; and determining a displacement for each scattering point of the object relative to a fiducial position on the propagation axis of the incident beam on a basis of the detected energy of the scattered radiation.

In other embodiments of the present invention, the method may also have a step of characterizing the object on the basis of a measure of attenuation between an identified scattering point and an identified detector. There may be additional steps of moving the object relative to the incident beam, or of varying the position or orientation of the incident beam relative to the object. In particular, the source and the plurality of detector elements may be rotated relative to the object.

BRIEF DESCRIPTION OF THE DRAWINGS

The foregoing features of the invention will be more readily understood by reference to the following detailed description taken with the accompanying drawings.

DETAILED DESCRIPTION OF EMBODIMENTS OF THE INVENTION

Limitations of the apparatus and methods of SAT as current known and practiced in the art may be advantageously overcome in accordance with embodiments of the present invention now described. In accordance with preferred embodiments of the present invention, a collimated monochromatic radiation source (e.g., a radioactive source instead of an x-ray tube or other x-ray generating device, or a source filtered to emit substantially within a narrow band of energies) and a plurality—typically a pair—of uncollimated, energy-resolving detectors. As will be shown, the advantages of the invention are that all materials illuminated by the beam can be interrogated simultaneously, instead of restriction to a single sub-volume, as in the case of the prior art SAT techniques. This means that the precise location (along the beam) of the suspect region need not be known beforehand. A tradeoff incurred in practicing methods in accordance with the present invention is that interrogation times may be long due to the typically lower intensity of radioactive sources (even intense ones) compared with x-ray tubes or linear accelerators.

Figure 1:
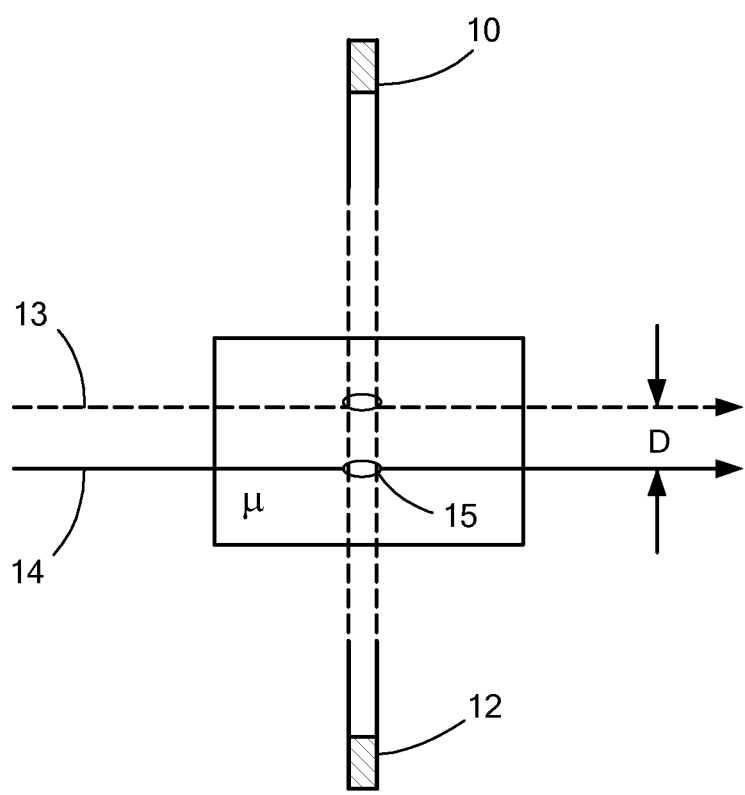
FIG. 1 depicts a prior art Scatter Attenuation Tomography system employing an x-ray tube source and collimated scatter detectors.

The previously described SAT technique is shown in FIG. 1. The previously described technique uses the scatter signal detected in each of the two collimated detectors 10 and 12 for each of the two beam positions 13 and 14 to determine the linear attenuation coefficient μ (or SAT number $N_{SAT}$) of the scattered radiation in the material between the two orange voxels. The SAT number is given by $$N_{SAT}(E) = \mu(E) = \ln\left[\frac{L_1}{L_2} \cdot \frac{R_2}{R_1}\right]/2D, \quad \text{(Eq. 1)}$$

where D is the distance between the two voxels, $L_1$ and $L_2$ are the number of detected scattered x-rays (or an equivalent measure) in the left detector 10 for beam positions 1 and 2, and $R_1$ and $R_2$ are corresponding measures of scattered x-rays in the right detector 12.

The previously described SAT technique is a point interrogation method that only characterizes one small sub-region of an object, namely voxel 15 giving rise to scatter detected in the left and right detector elements.

Figure 2:
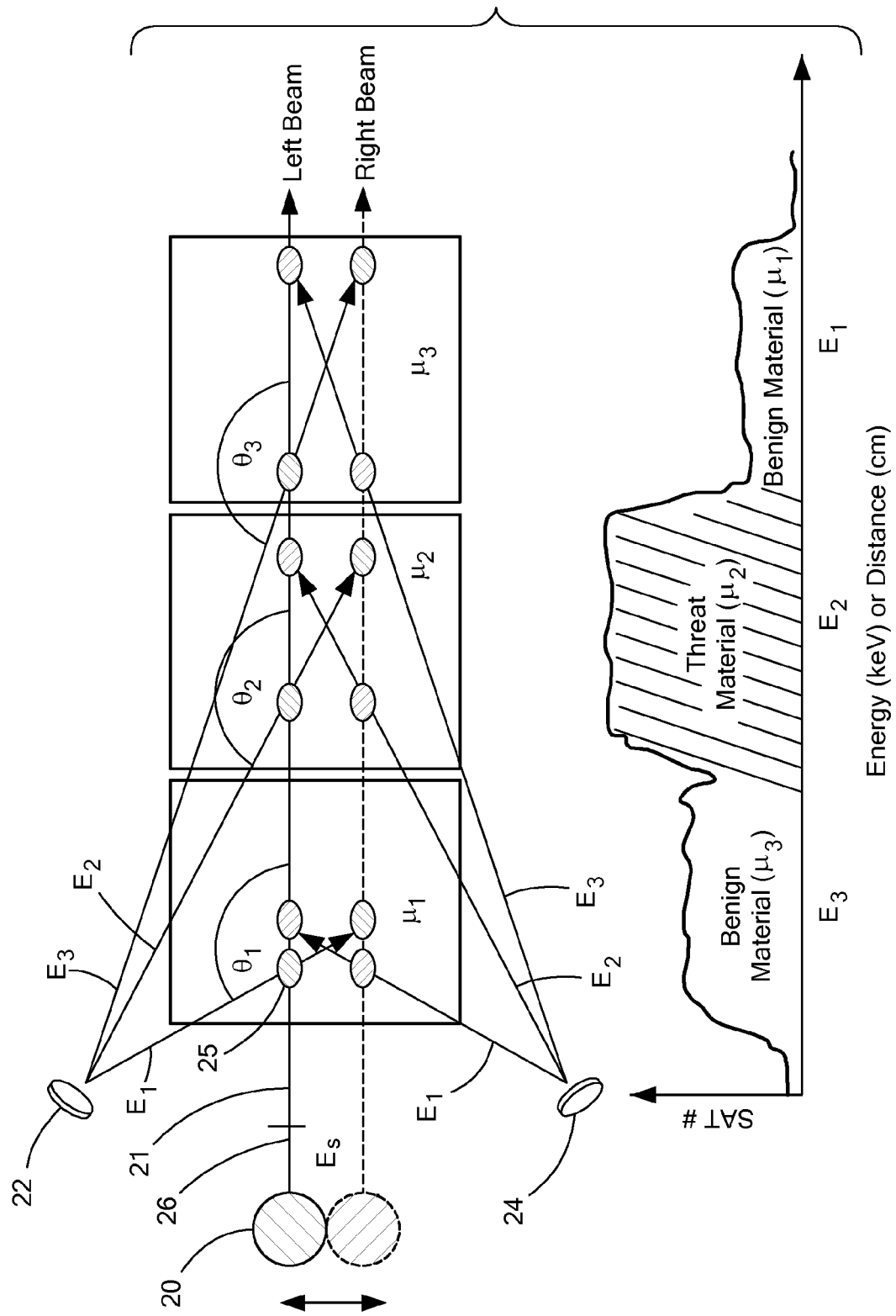
FIG. 2 is a schematic depiction of an SAT technique using a radioactive source as the source of monochromatic radiation and uncollimated energy-resolving detectors, in accordance with an embodiment of the present invention.

In contradistinction to the previously described SAT technique, methods in accordance with the present invention, as now described with reference to FIG. 2, use a collimated radioactive source 20 and two substantially uncollimated detectors 22 and 24, which are preferably energy-resolving, as discussed below. Within the scope of the present invention, detectors 22 and 24 may be collimated to some degree, but only in order to restrict the detection of multiply scattered radiation, and any detector collimation should still provide for detection of singly scattered radiation from many points along the radiation beam. Collimated source 20 creates an incident beam 21 which may be steered by a beam steerer such as a moving shutter, for example, or by moving the source by means of any manner of actuator.

By using a source 20 from which x-rays of a substantially single monochromatic energy $E_s$ are emitted, the energy ($E_1$, $E_2$, $E_3$ ..., or, generally, $E_f$) of the detected x-rays which are scattered out of the beam can be used to determine where along the beam they were scattered from, based on considerations of conservation of momentum and energy. For example, an x-ray which is scattered out of incident beam 21 through an angle Θ will have a final energy $E_f$ after being scattered given by:

$$E_f = \frac{E_s}{\left[1 + \frac{E_s}{m_e}(1 - \cos\Theta)\right]}, \quad \text{(Eqn. 2)}$$

where $E_s$ is the x-ray energy emitted by the source in keV and $m_e$ is the mass of an electron (511 keV). By algebraic rearrangement, if the final energy has been measured, the scatter angle is given by:

$$\Theta = \cos^{-1} m_e \left[\frac{1}{m_e} + \frac{1}{E_s} - \frac{1}{E_f}\right]. \quad \text{(Eqn. 3)}$$

The scatter angle Θ can then be used to calculate the distance X of the point of scatter relative to a fiducial origin X=0, designated by numeral 26, along the beam:

$$X = L \tan[\theta - 90] \quad \text{(Eqn. 4)}$$

where L is the perpendicular distance of the detector from the beam plane and X=0 in the plane of the detector.

If the detectors 22 and 24 are energy-resolving detectors, the scatter point 25 of the detected scattered x-rays can be determined from Eqns. 3 and 4. The scattered x-rays can then be assigned to voxels such as those shown located on the two beams in FIG. 2, depending on the location of their scatter point.

Figure 3:
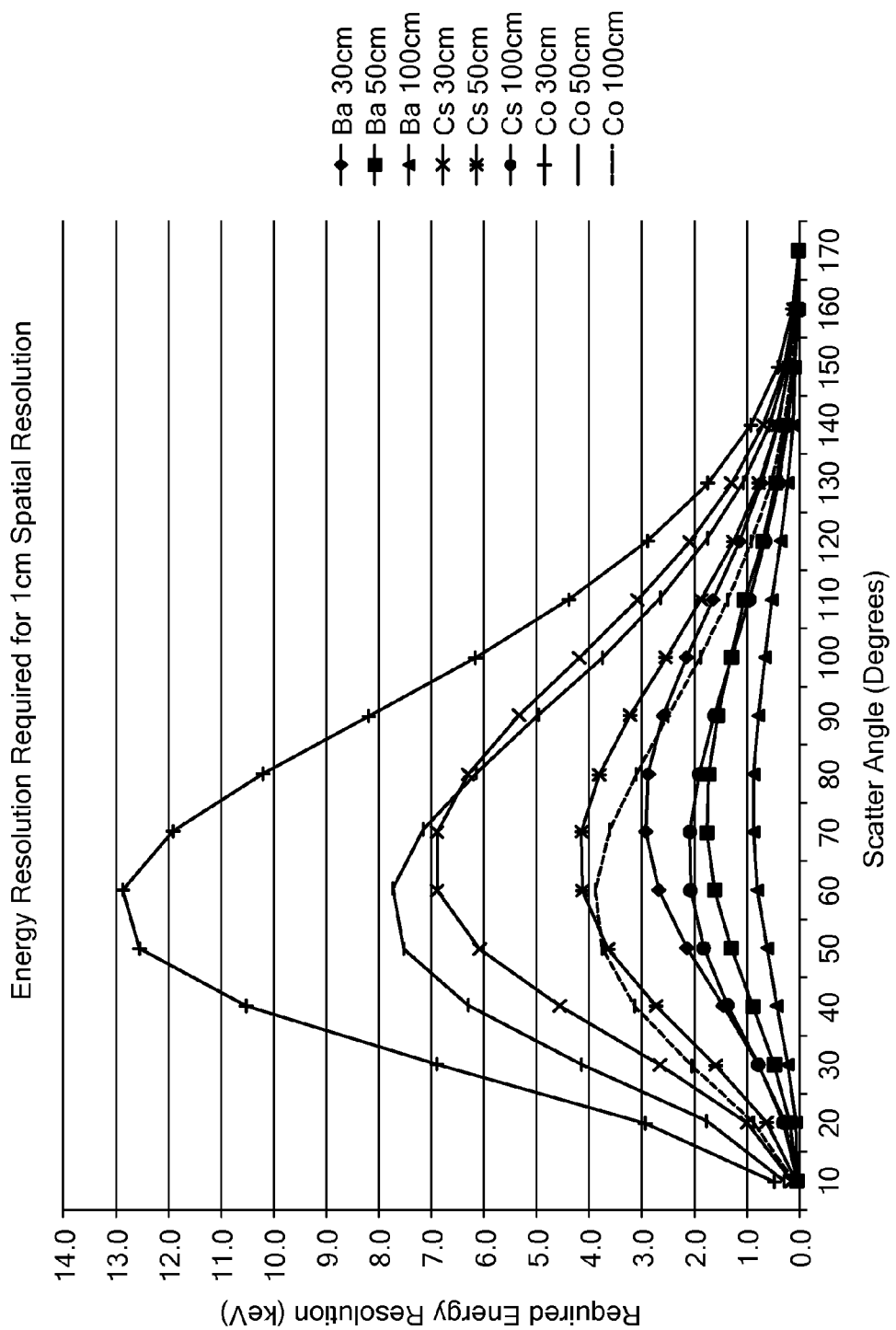
FIG. 3 plots required energy resolution to discriminate two x-rays with scatter points 1 cm apart for Ba-133, Cs-137, and Co-60 sources, with the detectors positioned 30, 50, and 100 cm from the beam plane, in accordance with an embodiment of the present invention.

FIG. 3 show the energy resolution that is required to discriminate two x-rays with scatter points along the beam separated by 1 cm, as a function of scatter angle. For example, for a forward scatter angle of 60 degrees, a beam to detector distance of 30 cm, and a cobalt-60 source with an x-ray energy of 1.2 MeV, the two x-rays will have energies separated by almost 13 keV, well within the energy resolution of a high-purity germanium detector (HpGe), which can be as great as about 0.5 keV at 662 keV. At a backward scatter angle of 135 degrees, however, the energy separation between the two x-rays for the same radioactive source and same detector distance has decreased to only about 1.5 keV.

Once the detected scattered x-rays have been binned according to their final energy (or scatter point), the SAT number of all the voxels along the beams can be calculated. This provides a set of data analogous to the data obtained in prior art SAT analysis, and allows discrimination among benign and threat materials on the basis of SAT number, as shown in the plot of FIG. 2. The voxel size (and hence the spatial resolution of the SAT characterization of the object being analyzed) depends upon the available statistics, which in turn depends on the source strength, the scan time, the detector size, and the distance from the object to the detectors. By calculating the attenuation of penetrating radiation between pairs of scattering voxels, a tomographic image is obtained characterizing the three-dimensional distribution of attenuation, in a direction within the object having a component transverse to the incident beam, of one or more energies of penetrating radiation, and thus of various material characteristics.

Figure 4:
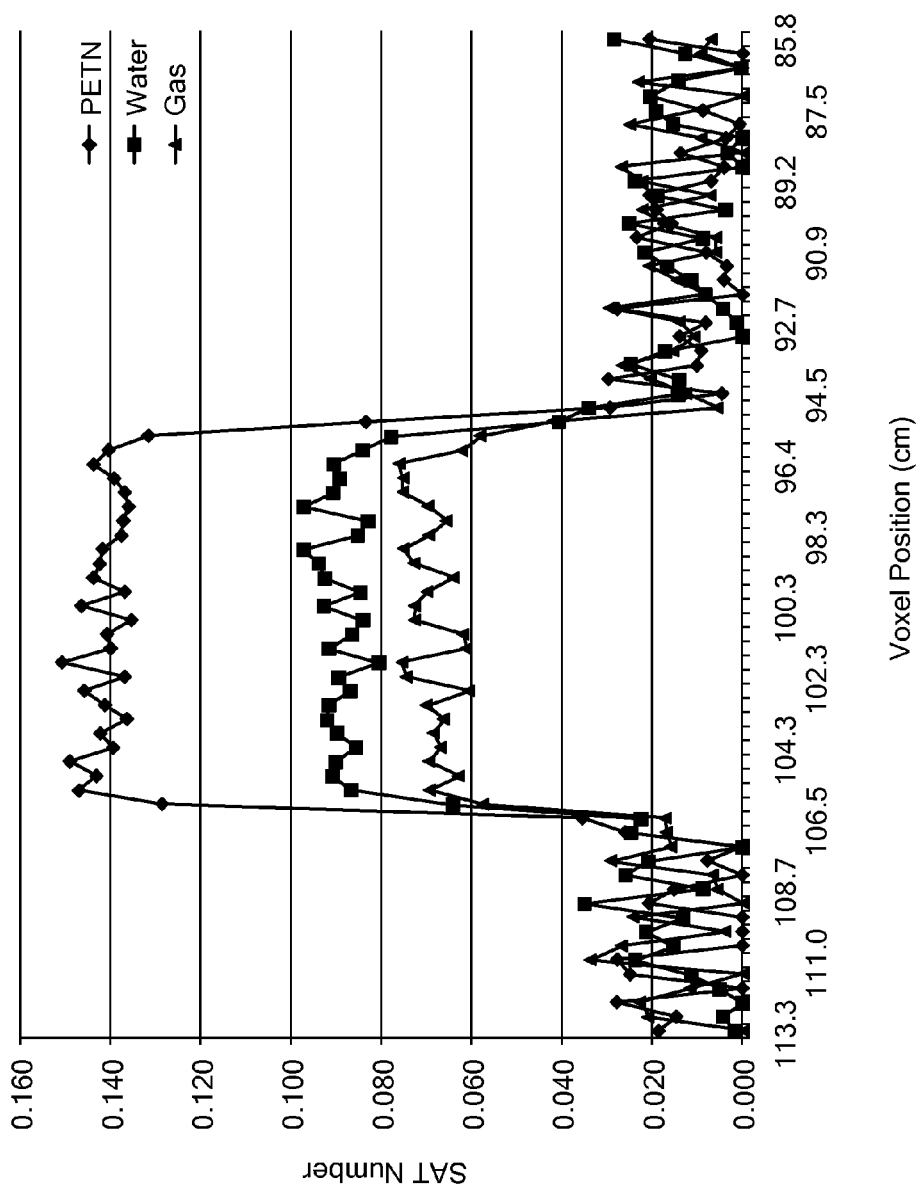
FIG. 4 plots SAT number vs. voxel position in a simulation of PETN, water, and gasoline concealed within cotton cargo for a 1.2 MeV Co-60 source.

The results of computer simulations for a 1.2 MeV Co-60 source and a 10-cm cube of various materials concealed at the center of a 1-m diameter sphere of low-density cotton are presented in FIG. 4. It can be seen that the measured SAT numbers accurately reflect the increasing density of the concealed materials, from low density gasoline ($\rho=0.75$ g/cc) to high density PETN explosive ($\rho=1.6$ g/cc)

Embodiments of the present invention provide novel methods for characterizing or identifying concealed (or non-concealed) materials without requiring access to the far side of the object. The object may be moved relative to the source, such as by any manner of conveyor, and the object may be rotated with respect to the source and detectors, or the source and detectors may be rotated relative to the object.

In accordance with an alternate embodiment of the invention, a scatter attenuation tomography system with a radioactive source is mounted on a bomb disposal robot, and may be used to verify the presence of an explosive material. In a yet further embodiment of the present invention, a small radioactive source is employed in a hand-held SAT system for the inspection of suspect items simply by pointing the device at the item. Among numerous applications of the invention, one embodiment entails a method for characterizing rock or soil in mining or drilling applications. All such applications are within the scope of the present invention as claimed.

All of the heretofore described embodiments of the invention are intended to be merely exemplary and numerous variations and modifications will be apparent to those skilled in the art. All such variations and modifications are intended to be within the scope of the present invention as defined in any appended claims.

What is claimed is:

1. An x-ray inspection system for characterizing an object, the x-ray inspection system comprising:
   a source for generating an incident beam of substantially monochromatic penetrating radiation, the incident beam characterized by a propagation axis and a source energy;
   a plurality of detector elements disposed about the beam of penetrating radiation, each detector element generating a detector signal characterizing a detected energy of scattered radiation;
   a processor input adapted to receive the detector signal characterizing radiation scattered from at least one scattering point of the object illuminated by the incident beam; and
   a processor adapted to determine a displacement for each scattering point of the object relative to a fiducial position on the propagation axis of the incident beam on a basis of the detected energy of the scattered radiation.

2. An x-ray inspection system in accordance with claim 1, wherein the processor is further adapted to characterize the object on the basis of a measure of attenuation between an identified scattering point and an identified detector.

3. An x-ray inspection system in accordance with claim 1, wherein the source for generating an incident beam is a radioactive source.

4. An x-ray inspection system in accordance with claim 1, further comprising a beam steerer for varying at least one of an orientation and a position of the incident beam relative to the object.

5. An x-ray inspection system in accordance with claim 4, wherein the beam steerer includes a moving shutter.

6. An x-ray inspection system in accordance with claim 4, wherein the beam steerer includes an actuator for moving the source.

7. An x-ray inspection system in accordance with claim 1, wherein at least one of a plurality of detector elements is disposed to the side of the object with respect to the incident beam.

8. An x-ray inspection system in accordance with claim 1, wherein the plurality of detector elements are energy-selective.

9. A method for characterizing an object on the basis of a measure of attenuation in a direction having a transverse component to an incident beam, the method comprising:
   generating an incident beam of substantially monochromatic penetrating radiation, the incident beam characterized by a propagation axis and a source energy;
   detecting radiation scattered by the object by means of a plurality of detector elements disposed about the beam of penetrating radiation, each detector element generating a detector signal characterizing a detected energy of scattered radiation;
   receiving the detector signal characterizing radiation scattered from at least one scattering point of the object illuminated by the incident beam; and
   determining a displacement for each scattering point of the object relative to a fiducial position on the propagation axis of the incident beam on a basis of the detected energy of the scattered radiation.

10. A method in accordance with claim 9, further comprising
   characterizing the object on the basis of a measure of attenuation between an identified scattering point and an identified detector.

11. A method in accordance with claim 9, further comprising moving the object relative to the incident beam.

12. A method in accordance with claim 9, further comprising varying an orientation of the incident beam relative to the object.

13. A method in accordance with claim 9, further comprising moving the incident beam relative to the object.

14. A method in accordance with claim 9, further comprising steering the plurality of detector elements independently relative to the object.

15. A method in accordance with claim 9, further comprising rotating the source and the plurality of detector elements relative to the object.

\* \* \* \* \*